(12) United States Patent
Nakamura et al.

(10) Patent No.: US 11,923,069 B2
(45) Date of Patent: Mar. 5, 2024

(54) MEDICAL DOCUMENT CREATION SUPPORT APPARATUS, METHOD AND PROGRAM, LEARNED MODEL, AND LEARNING APPARATUS, METHOD AND PROGRAM

(71) Applicant: FUJIFILM Corporation, Tokyo (JP)

(72) Inventors: Keigo Nakamura, Tokyo (JP); Shinnosuke Hirakawa, Tokyo (JP); Yohei Momoki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 765 days.

(21) Appl. No.: 17/074,543

(22) Filed: Oct. 19, 2020

(65) Prior Publication Data

US 2021/0035676 A1 Feb. 4, 2021

Related U.S. Application Data

(63) Continuation of application No. PCT/JP2019/014707, filed on Apr. 2, 2019.

(30) Foreign Application Priority Data

Apr. 24, 2018 (JP) ................... 2018-083079

(51) Int. Cl.
*G16H 30/40* (2018.01)
*G06F 18/21* (2023.01)
(Continued)

(52) U.S. Cl.
CPC ............. *G16H 30/40* (2018.01); *G06F 18/21* (2023.01); *G06F 40/10* (2020.01); *G06N 20/00* (2019.01);
(Continued)

(58) Field of Classification Search
CPC ........ G16H 30/40; G16H 15/00; G16H 30/20; G06F 18/21; G06F 40/10; G06F 18/2413;
(Continued)

(56) References Cited

U.S. PATENT DOCUMENTS

2005/0107690 A1  5/2005  Soejima
2009/0076853 A1  3/2009  Sagawa
(Continued)

FOREIGN PATENT DOCUMENTS

JP  2005148990  6/2005
JP  2009070201  4/2009
(Continued)

OTHER PUBLICATIONS

Kudo (JP 2016-133821); Jul. 25, 2016; Cited portions of English Translation (Year: 2016).*

(Continued)

*Primary Examiner* — Neil R McLean
(74) *Attorney, Agent, or Firm* — JCIPRNET

(57) ABSTRACT

A feature information acquisition unit acquires the first feature information on the first medical image and second feature information on the second medical image having an imaging time different from an imaging time of the first medical image. A sentence creation unit compares the first feature information and the second feature information generated by the feature information acquisition unit, and creates a sentence representing a change between the first medical image and the second medical image. A display control unit causes the display unit to display a sentence representing a change.

11 Claims, 9 Drawing Sheets

(51) Int. Cl.
    *G06F 40/10*     (2020.01)
    *G06N 20/00*     (2019.01)
    *G06T 7/00*     (2017.01)
    *G06V 10/20*     (2022.01)
    *G06V 10/40*     (2022.01)
    *G06V 10/75*     (2022.01)
    *G06V 10/764*     (2022.01)
    *G06V 10/82*     (2022.01)
    *G16H 15/00*     (2018.01)
    *G16H 30/20*     (2018.01)

(52) U.S. Cl.
    CPC .......... *G06T 7/0016* (2013.01); *G06V 10/255* (2022.01); *G06V 10/40* (2022.01); *G06V 10/751* (2022.01); *G06V 10/764* (2022.01); *G06V 10/82* (2022.01); *G16H 15/00* (2018.01); *G16H 30/20* (2018.01); *G06T 2207/20081* (2013.01); *G06T 2207/20084* (2013.01); *G06V 2201/03* (2022.01)

(58) Field of Classification Search
    CPC ........ G06F 40/56; G06N 20/00; G06N 3/044; G06N 3/08; G06T 7/0016; G06T 2207/20081; G06T 2207/20084; G06T 2200/24; G06T 2207/10072; G06T 2207/30064; G06V 10/255; G06V 10/40; G06V 10/751; G06V 10/764; G06V 10/82; G06V 2201/03
    USPC ....................................................... 382/128
See application file for complete search history.

(56) References Cited

U.S. PATENT DOCUMENTS

| | | |
|---|---|---|
| 2010/0189366 A1 | 7/2010 | Iizuka et al. |
| 2016/0350919 A1 | 12/2016 | Steigauf et al. |
| 2017/0293725 A1 | 10/2017 | Liu et al. |
| 2018/0204325 A1 | 7/2018 | Steigauf et al. |
| 2019/0325300 A1* | 10/2019 | Xu .................. G16H 15/00 |

FOREIGN PATENT DOCUMENTS

| | | |
|---|---|---|
| JP | 2009082443 | 4/2009 |
| JP | 2016133821 | 7/2016 |

OTHER PUBLICATIONS

"International Search Report (Form PCT/ISA/210) of PCT/JP2019/014707," dated Jun. 25, 2019, with English translation thereof, pp. 1-5.

"Written Opinion of the International Searching Authority (Form PCT/ISA/237) of PCT/JP2019/014707," dated Jun. 25, 2019, with English translation thereof, pp. 1-9.

Office Action of Japan Counterpart Application, with English translation thereof, dated Oct. 26, 2021, pp. 1-5.

* cited by examiner

MEDICAL DOCUMENT CREATION SUPPORT APPARATUS, METHOD AND PROGRAM, LEARNED MODEL, AND LEARNING APPARATUS, METHOD AND PROGRAM

CROSS REFERENCE TO RELATED APPLICATIONS

The present application is a Continuation of PCT International Application No. PCT/JP2019/014707 filed on Apr. 2, 2019, which claims priority under 35 U.S.C. § 119(a) to Japanese Patent Application No. 2018-083079 filed on Apr. 24, 2019. Each of the above applications is hereby expressly incorporated by reference, in its entirety, into the present application.

BACKGROUND

Technical Field

The present disclosure relates to a medical document creation support apparatus, a method and a program, a learned model, and a learning apparatus, a method and a program that support a creation of medical documents such as an interpretation report.

Related Art

In recent years, advances in medical apparatuses, such as computed tomography (CT) apparatuses and magnetic resonance imaging (MRI) apparatuses, have enabled image diagnosis using high-resolution medical images with higher quality. In particular, since a region of a lesion can be accurately specified by image diagnosis using CT images, MRI images, and the like, appropriate treatment can be performed based on the specified result.

A medical image is analyzed by computer-aided diagnosis (CAD) using a discriminator in which learning is performed by deep learning or the like, regions, positions, volumes, and the like of lesions included in the medical image are extracted, and these are acquired as the analysis result. The analysis result generated by analysis processing in this manner is stored in a database so as to be associated with examination information, such as a patient name, gender, age, and a modality that has acquired the medical image, and provided for diagnosis. At this time, a radiology technician who acquired medical images determines a radiologist according to the medical image and informs the determined radiologist that the medical image and the CAD analysis result are present. The radiologist interprets the medical image with reference to the transmitted medical image and analysis result and creates an interpretation report in his or her own interpretation terminal.

In a case where medical documents such as an interpretation report are created, a comparative interpretation is performed by referring to a past medical image and a past interpretation report of a subject who acquired a target medical image, and changes in a lesion and the like are often described in the interpretation report. For this reason, various methods have been proposed for referring to a finding sentence and the like described in a past interpretation report (hereinafter referred to as a past report) at the time of creating a current interpretation report (hereinafter referred to as a current report). For example, JP2009-070201A discloses a method for easily creating the interpretation report by copying comments described in the past report, creating information related to a current image from information related to a past image, and creating a template for creating the current report.

On the other hand, a radiologist interprets a large number of medical images and creates an interpretation report. In particular, in a case of performing comparative interpretation, it is necessary to refer to more medical images and interpretation reports. It is desired to reduce a burden on the radiologist in a case of describing results of such comparative interpretation in the interpretation report.

SUMMARY OF THE INVENTION

The present disclosure has been made in view of the above circumstances, and an object of the present disclosure is to reduce the burden on operators, such as a radiologist, in a case of creating medical documents such as an interpretation report on a medical image including the comparison results of a plurality of medical images.

The medical document creation support apparatus according to the present disclosure comprises a feature information acquisition unit that acquires first feature information on a first medical image and second feature information on a second medical image having an imaging time different from an imaging time of the first medical image, and a sentence creation unit that compares the first feature information and the second feature information to create a sentence representing a change between the first medical image and the second medical image.

It should be noted that in the medical document creation support apparatus according to the present disclosure, the feature information acquisition unit may acquire first text data representing at least one finding based on the first medical image as the first feature information, and acquires second text data representing at least one finding based on the second medical image as the second feature information.

In addition, in the medical document creation support apparatus according to the present disclosure, the feature information acquisition unit may analyze at least one of the first medical image or the second medical image to acquire the first text data and the second text data.

In addition, in the medical document creation support apparatus according to the present disclosure, the sentence creation unit may have a learned model in which machine learning is performed so as to output the sentence representing the change on the basis of the first text data and the second text data.

In addition, in the medical document creation support apparatus according to the present disclosure, the learned model may have a plurality of input layers to which each of at least one finding based on the first medical image and at least one finding based on the second medical image is input, and a plurality of output layers to which an output from the input layers is input and which output the sentence representing the change, in which the learned model being configured by a neural network in which weight coefficients between the plurality of input layers and the plurality of output layers and mutual weight coefficients between the plurality of output layers are learned, and causing a computer to output the sentence representing the change so as to sequentially output a plurality of words constituting the sentence representing the change on the basis of a correspondence relationship between at least one finding based on the first medical image and at least one finding based on the second medical image in a case where the first text data and the second text data are input, the learned model.

In addition, in the medical document creation support apparatus according to the present disclosure, the feature information acquisition unit may acquire a feature quantity of the first medical image as the first feature information, and acquires a feature quantity of the second medical image as the second feature information.

In addition, the medical document creation support apparatus according to the present disclosure may further comprise a display control unit that displays the sentence representing the change on a display unit.

A learned model according to the present disclosure comprises a plurality of input layers to which each of at least one finding based on a first medical image and at least one finding based on a second medical image having an imaging time different from an imaging time of the first medical image is input, and a plurality of output layers to which an output from the input layers is input and which output a sentence representing a change between the first medical image and the second medical image, in which the learned model is configured by a neural network in which weight coefficients between the plurality of input layers and the plurality of output layers are learned, and in a case where the finding based on the first medical image and the finding based on the second medical image are input, the learned model causes a computer to output the sentence representing the change so as to sequentially output a plurality of words constituting the sentence representing the change on the basis of a correspondence relationship between at least one finding based on the first medical image and at least one finding based on the second medical image.

A learning apparatus according to the present disclosure is a learning apparatus for performing learning on a neural network to generate a learned model, the neural network having a plurality of input layers to which each of at least one finding based on a first medical image and at least one finding based on a second medical image having an imaging time different from an imaging time of the first medical image is input, and a plurality of output layers to which an output from the input layers is input and which output a sentence representing a change between the first medical image and the second medical image, and the learning apparatus comprises a learning unit that performs learning for setting weight coefficients between the plurality of input layers and the plurality of output layers in the neural network so as to sequentially output a plurality of words constituting the sentence representing the change on the basis of a correspondence relationship between at least one finding based on the first medical image and at least one finding based on the second medical image in a case where the finding based on the first medical image and the finding based on the second medical image are input.

A medical document creation support method according to the present disclosure acquires first feature information on a first medical image and second feature information on a second medical image having an imaging time different from an imaging time of the first medical image, and compares the first feature information and the second feature information to create a sentence representing a change between the first medical image and the second medical image.

A learning method according to the present disclosure is a learning method for performing learning on a neural network to generate a learned model, the neural network having a plurality of input layers to which each of at least one finding based on a first medical image and at least one finding based on a second medical image having an imaging time different from an imaging time of the first medical image is input, and a plurality of output layers to which an output from the input layers is input and which output a sentence representing a change between the first medical image and the second medical image, and the learning method performs learning for setting weight coefficients between the plurality of input layers and the plurality of output layers in the neural network so as to sequentially output a plurality of words constituting the sentence representing the change on the basis of a correspondence relationship between at least one finding based on the first medical image and at least one finding based on the second medical image in a case where the finding based on the first medical image and the finding based on the second medical image are input.

It should be noted that the medical document creation support method according to the present disclosure may be provided as a program for causing a computer to execute the method.

In addition, the learning method according to the present disclosure may be provided as a program for causing a computer to execute the method.

Another medical document creation support apparatus according to the present disclosure comprises a memory that stores instructions for causing a computer to execute the apparatus, and a processor that is configured to execute the stored instructions, the processor acquiring first feature information on a first medical image and second feature information on a second medical image having an imaging time different from an imaging time of the first medical image, and comparing the first feature information and the second feature information to create a sentence representing a change between the first medical image and the second medical image.

A learning apparatus according to the present disclosure is another learning apparatus for causing a computer to execute a process of performing learning on a neural network to generate a learned model, the neural network having a plurality of input layers to which each of at least one finding based on a first medical image and at least one finding based on a second medical image having an imaging time different from an imaging time of the first medical image is input, and a plurality of output layers to which an output from the input layers is input and which output a sentence representing a change between the first medical image and the second medical image, and the learning apparatus comprises a memory that stores instructions for causing a computer to execute the apparatus, and a processor that is configured to execute the stored instructions, the processor executing a learning process for setting weight coefficients between the plurality of input layers and the plurality of output layers in the neural network so as to sequentially output a plurality of words constituting the sentence representing the change on the basis of a correspondence relationship between at least one finding based on the first medical image and at least one finding based on the second medical image in a case where the finding based on the first medical image and the finding based on the second medical image are input.

According to the present disclosure, the first feature information on the first medical image and the second feature information on the second medical image having the imaging time different from the imaging time of the first medical image are acquired, and the first feature information and the second feature information are compared to create a sentence representing the change between the first medical image and the second medical image. For this reason, it is possible to reduce the burden on the operator of creating medical documents particularly in a case of performing comparative interpretation, and as a result, the operator can efficiently create the medical documents.

DETAILED DESCRIPTION

Figure 1:
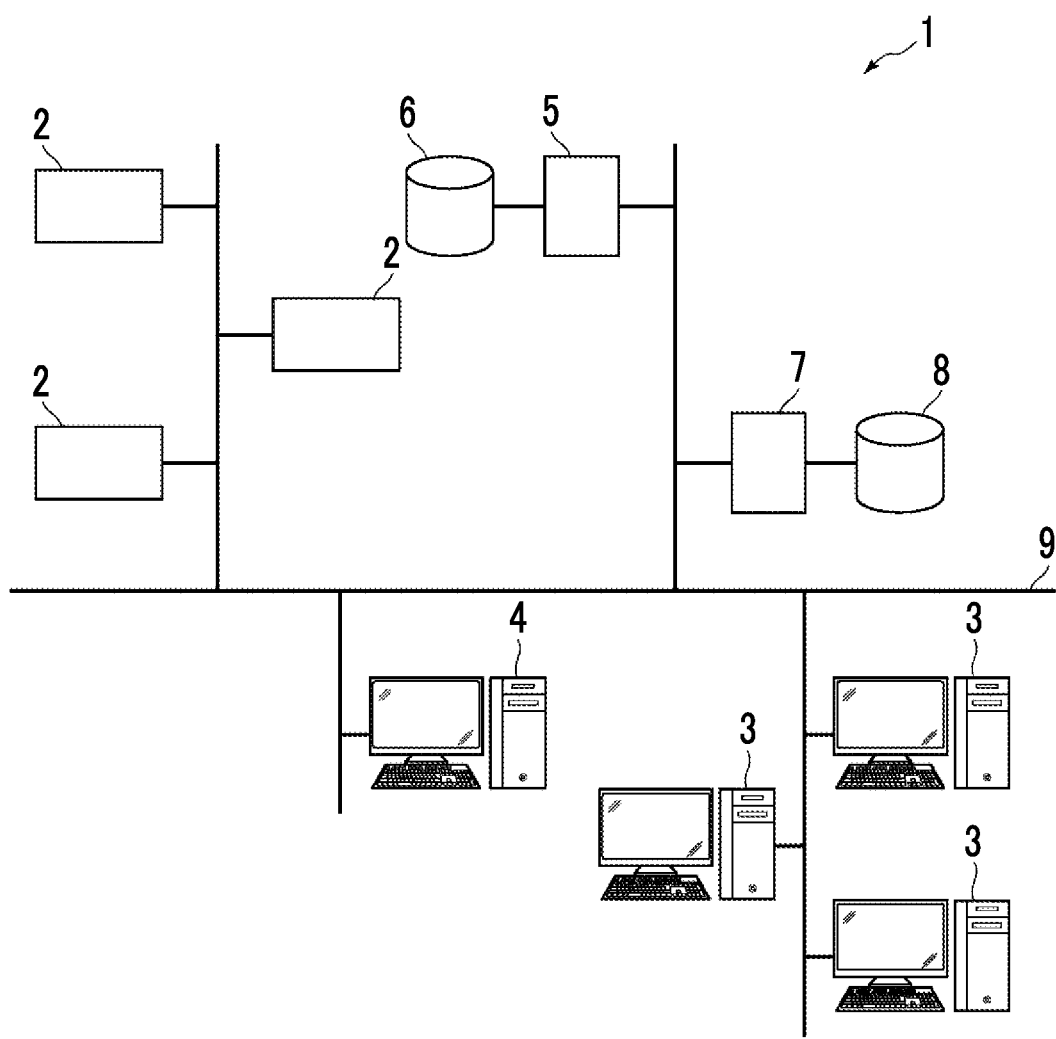
FIG. 1 is a diagram showing a schematic configuration of a medical information system to which a medical document creation support apparatus according to an embodiment of the present disclosure is applied.

Hereinafter, an embodiment of the present disclosure will be described with reference to the accompanying diagrams. FIG. 1 is a diagram showing a schematic configuration of a medical information system to which a medical document creation support apparatus, a learned model, and a learning apparatus according to an embodiment of the present disclosure is applied. A medical information system 1 shown in FIG. 1 is, on the basis of an examination order from a doctor in a medical department using a known ordering system, a system for performing imaging of an examination target part of a subject, storage of a medical image acquired by imaging, interpretation of a medical image by a radiologist and creation of an interpretation report, and viewing of an interpretation report by a doctor in a medical department of a request source and detailed observation of a medical image to be interpreted. As shown in FIG. 1, the medical information system 1 is configured to include a plurality of modalities (imaging apparatuses) 2, a plurality of interpretation workstations (WS) 3 that are interpretation terminals, a medical department workstation (WS) 4, an image server 5, an image database 6, an interpretation report server 7, and an interpretation report database 8 that are communicably connected to each other through a wired or wireless network 9.

Each apparatus is a computer on which an application program for causing each apparatus to function as a component of the medical information system 1 is installed. The application program is recorded on a recording medium, such as a digital versatile disc (DVD) or a compact disc read only memory (CD-ROM), and distributed, and is installed onto the computer from the recording medium. Alternatively, the application program is stored in a storage apparatus of a server computer connected to the network 9 or in a network storage so as to be accessible from the outside, and is downloaded and installed onto the computer as necessary.

A modality 2 is an apparatus that generates a medical image showing a diagnosis target part by imaging the diagnosis target part of the subject. Specifically, the modality 2 is a simple X-rays imaging apparatus, a CT apparatus, an MRI apparatus, a positron emission tomography (PET) apparatus, and the like. A medical image generated by the modality 2 is transmitted to the image server 5 and stored therein.

An interpretation WS 3 includes the medical document creation support apparatus, learned model, and learning apparatus according to the present embodiment. The configuration of the interpretation WS 3 will be described later.

A medical department WS 4 is a computer used by a doctor in a medical department to observe the details of an image, view an interpretation report, create an electronic medical record, and the like, and is configured to include a processing apparatus, a display apparatus such as a display, and an input apparatus such as a keyboard and a mouse. In the medical department WS 4, each processing, such as the creation of a medical record of a patient (electronic medical record), sending a request to view an image to the image server 5, display of an image received from the image server 5, automatic detection or highlighting of a lesion-like portion in an image, sending a request to view an interpretation report to the interpretation report server 7, and display of an interpretation report received from the interpretation report server 7, is performed by executing a software program for each processing.

The image server 5 is obtained by installing a software program for providing a function of a database management system (DBMS) on a general-purpose computer. The image server 5 comprises a storage for an image database 6. This storage may be a hard disk apparatus connected to the image server 5 by a data bus, or may be a disk apparatus connected to a storage area network (SAN) or a network attached storage (NAS) connected to the network 9. In a case where the image server 5 receives a request to register a medical image from the modality 2, the image server 5 registers the medical image in the image database 6 in a format for a database.

Image data of the medical image acquired by the modality 2 and accessory information are registered in the image database 6. The accessory information includes, for example, an image ID for identifying each medical image, a patient identification (ID) for identifying a subject, an examination ID for identifying an examination, a unique ID (UID: unique identification) allocated for each medical image, examination date and examination time at which the medical image is generated, the type of a modality used in an examination for acquiring a medical image, patient information such as the name, age, and gender of a patient, an examination part (imaging part), imaging information (an imaging protocol, an imaging sequence, an imaging method, imaging conditions, the use of a contrast medium, and the like), and information such as a series number or a collection number in a case where a plurality of medical images are acquired in one examination.

In addition, in a case where a viewing request from the interpretation WS 3 is received through the network 9, the image server 5 searches for a medical image registered in the image database 6 and transmits the searched medical image to the interpretation WS 3 that is a request source.

The interpretation report server 7 has a software program for providing a function of a database management system to a general-purpose computer. In a case where the interpretation report server 7 receives a request to register an interpretation report from the interpretation WS 3, the interpretation report server 7 registers the interpretation report in the interpretation report database 8 in a format for a database. In a case where a request to search for an interpretation report is received, the interpretation report is searched for from the interpretation report database 8.

In the interpretation report database 8, for example, an interpretation report is registered in which information, such as an image ID for identifying a medical image to be interpreted, a radiologist ID for identifying an image diagnostician who performed the interpretation, a lesion name, position information of a lesion, findings and confidence of the findings, is recorded.

The network 9 is a wired or wireless local area network that connects various apparatuses in a hospital to each other. In a case where the interpretation WS 3 is installed in another hospital or clinic, the network 9 may be configured to connect local area networks of respective hospitals through the internet or a dedicated circuit. In any case, it is preferable that the network 9 is configured to be able to realize high-speed transmission of medical images, such as an optical network.

Hereinafter, the interpretation WS 3 according to the present embodiment will be described in detail. The interpretation WS 3 is a computer used by a radiologist of a medical image to interpret the medical image and create the interpretation report, and is configured to include a processing apparatus, a display apparatus such as a display, and an input apparatus such as a keyboard and a mouse. In the interpretation WS 3, each processing, such as making a request to view a medical image to the image server 5, various kinds of image processing on a medical image received from the image server 5, display of a medical image, analysis processing on a medical image, highlighting of a medical image based on the analysis result, creation of an interpretation report based on the analysis result, support for the creation of an interpretation report, making a request to register an interpretation report and a request to view an interpretation report to the interpretation report server 7, and display of an interpretation report received from the interpretation report server 7, is performed by executing a software program for each processing. It should be noted that since processing other than processing performed by the medical document creation support apparatus, learned model, and learning apparatus of the present embodiment, among these processing, are performed by a known software program, the detailed description thereof will be omitted herein. In addition, the processing other than the processing performed by the medical document creation support apparatus of the present embodiment may not be performed in the interpretation WS 3, and a computer that performs the processing may be separately connected to the network 9, and requested processing on the computer may be performed according to a processing request from the interpretation WS 3.

An interpretation WS 3 includes the medical document creation support apparatus, learned model, and learning apparatus according to the present embodiment. Therefore, a medical document creation support program, learned model, and learning program according to the present embodiment are installed on the interpretation WS 3. The medical document creation support program, learned model, and learning program are recorded on a recording medium, such as a DVD or a CD-ROM, and distributed, and are installed onto the interpretation WS 3 from the recording medium. Alternatively, the medical document creation support program is stored in a storage apparatus of a server computer connected to the network or in a network storage so as to be accessible from the outside, and is downloaded and installed onto the interpretation WS 3 as necessary.

Figure 2:
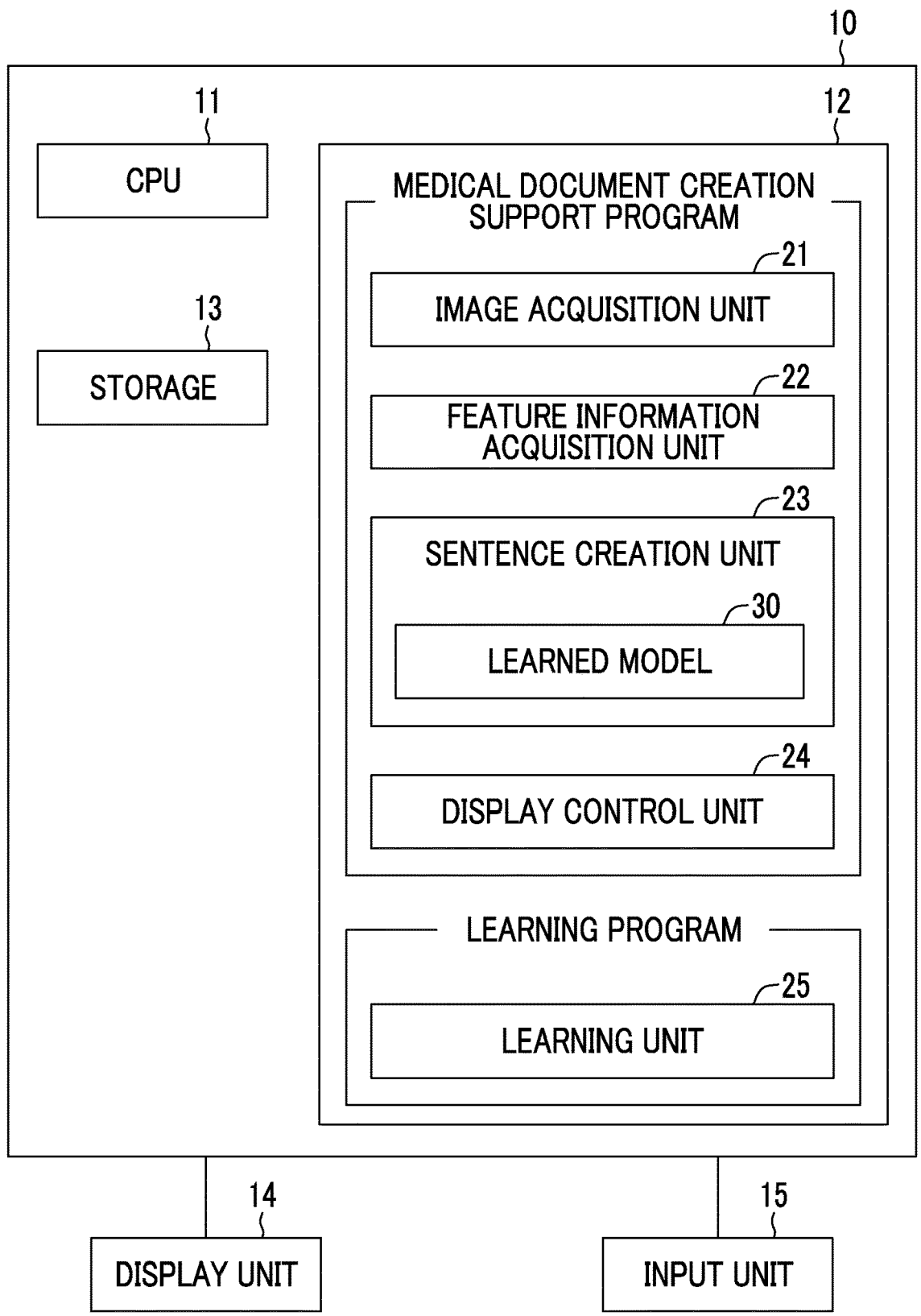
FIG. 2 is a diagram showing a schematic configuration of a medical document creation support apparatus according to the first embodiment.

FIG. 2 is a diagram showing the schematic configuration of a medical document creation support apparatus according to the first embodiment of the present disclosure that is realized by installing the medical document creation support program, learned model, and learning program. It should be noted that in the first embodiment, a medical document creation support apparatus includes the learned model and the learning apparatus. Therefore, FIG. 2 shows only the medical document creation support apparatus. As shown in FIG. 2, the medical document creation support apparatus 10 comprises a central processing unit (CPU) 11, a memory 12, and a storage 13 as the configuration of a standard computer. A display apparatus (hereinafter, referred to as a display unit) 14, such as a liquid crystal display, and an input apparatus (hereinafter, referred to as an input unit) 15, such as a keyboard and a mouse, are connected to the medical document creation support apparatus 10.

The storage 13 consists of a storage device, such as a hard disk or a solid state drive (SSD). Medical images and various kinds of information including information necessary for processing of the medical document creation support apparatus 10, which are acquired from the image server 5 through the network 9, are stored in the storage 13.

The medical document creation support program, learned model, and learning program are stored in the memory 12. The medical document creation support program specifies, as processing to be executed by a CPU 11, image acquisition processing of acquiring a first medical image and a second medical image having the imaging time different from each other, feature information acquisition processing of acquiring the first feature information on the first medical image and the second feature information on the second medical image, sentence creation processing of creating a sentence representing a change between the first medical image and the second medical image by comparing the first feature information on the first medical image and the second feature information on the second medical image, and display processing of displaying the sentence representing the change on a display unit 14. In addition, the learning program specifies, as processing to be executed by the CPU 11, a learning process of learning a neural network and generating a learned model included in the sentence creation unit as described later.

The computer functions as an image acquisition unit 21, a feature information acquisition unit 22, a sentence creation unit 23, and a display control unit 24 by the CPU 11 executing this processing according to the medical document creation support program. In addition, the computer functions as a learning unit 25 by the CPU 11 executing the learning process according to the learning program. It should be noted that in the present embodiment, the CPU 11 executes the function of each unit according to the medical document creation support program and learning program. However, as a general-purpose processor that executes software to function as various processing units, a programmable logic device (PLD) that is a processor whose circuit configuration can be changed after manufacturing, such as a field programmable gate array (FPGA), can be used in addition to the CPU 11. Alternatively, the processing of each unit may also be executed by a dedicated electric circuit that is a processor having a circuit configuration designed exclusively to execute specific processing, such as an application specific integrated circuit (ASIC).

One processing unit may be configured by one of various processors, or may be a combination of two or more processors of the same type or different types (for example, a combination of a plurality of FPGAs or a combination of a CPU and an FPGA). In addition, a plurality of processing units may be configured by one processor. As an example of configuring a plurality of processing units using one processor, first, as represented by a computer, such as a client and a server, there is a form in which one processor is configured by a combination of one or more CPUs and software and this processor functions as a plurality of processing units. Second, as represented by a system on chip (SoC) or the like, there is a form of using a processor that realizes the function of the entire system including a plurality of processing units with one integrated circuit (IC) chip. In this way, various processing units are formed using one or more of the above-mentioned various processors as hardware structures.

More specifically, the hardware structure of these various processors is an electrical circuit (circuitry) in the form of a combination of circuit elements, such as semiconductor elements.

The image acquisition unit 21 acquires, from an image storage server 3, each of the first medical image G1 and the second medical image G2 having different imaging times for the same subject. It should be noted that in a case where the first and second medical images G1 and G2 are already stored in the storage 13, the first and second medical images G1 and G2 may be acquired from the storage 13. In the following description, it is assumed that an imaging time of the first medical image G1 is earlier than an imaging time of the second medical image G2. In addition, the medical images G1 and G2 are CT images acquired by a CT apparatus, but the medical images G1 and G2 are not limited to this, and may be MRI images, PET images, or the like.

The feature information acquisition unit 22 acquires the first feature information C1 on the first medical image G1 and the second feature information C2 on the second medical image G2. First, the feature information acquisition unit 22 acquires the analysis result related to diseases and the like included in the first and second medical images G1 and G2 by analyzing the first and second medical images G1 and G2. For this purpose, the feature information acquisition unit 22 comprises a discriminator in which machine learning is performed so as to discriminate whether or not each pixel (voxel) in the first and second medical images G1 and G2 represents a lesion and the type of the lesion. In the present embodiment, the discriminator consists of a neural network in which deep learning is performed such that a plurality of types of lesions included in the first and second medical images G1 and G2 can be classified. In a case where the first and second medical images G1 and G2 are input, the discriminator in the feature information acquisition unit 22 performs learning to output the probability that each pixel (voxel) in the first and second medical images G1 and G2 is each of a plurality of lesions. Then, the discriminator obtains a lesion exceeding a predetermined threshold value and having the maximum probability for a certain pixel, and discriminates that the pixel is the pixel of the determined lesion.

It should be noted that the discriminator may be, for example, a support vector machine (SVM), a convolutional neural network (CNN), or a recurrent neural network (RNN) in addition to the neural network in which deep learning is performed.

In addition, the feature information acquisition unit 22 acquires the first feature information C1 on the first medical image G1 and the second feature information C2 on the second medical image G2 by using the discrimination result by the discriminator. Specifically, text data representing at least one of the findings of the first medical image G1 or the second first medical image G2, that is, the type of the lesion, the position of the lesion, the shape of the lesion, the size of the lesion, or the state of the lesion are generated as the first and second feature information C1 and C2. For example, in a case where the medical image includes a lung field and a lesion is found in the lung field, the feature information acquisition unit 22 generates text data including at least one of the position, type, size, or state of the lesion in the lung field as the findings as the first and second feature information C1 and C2.

Figure 3:
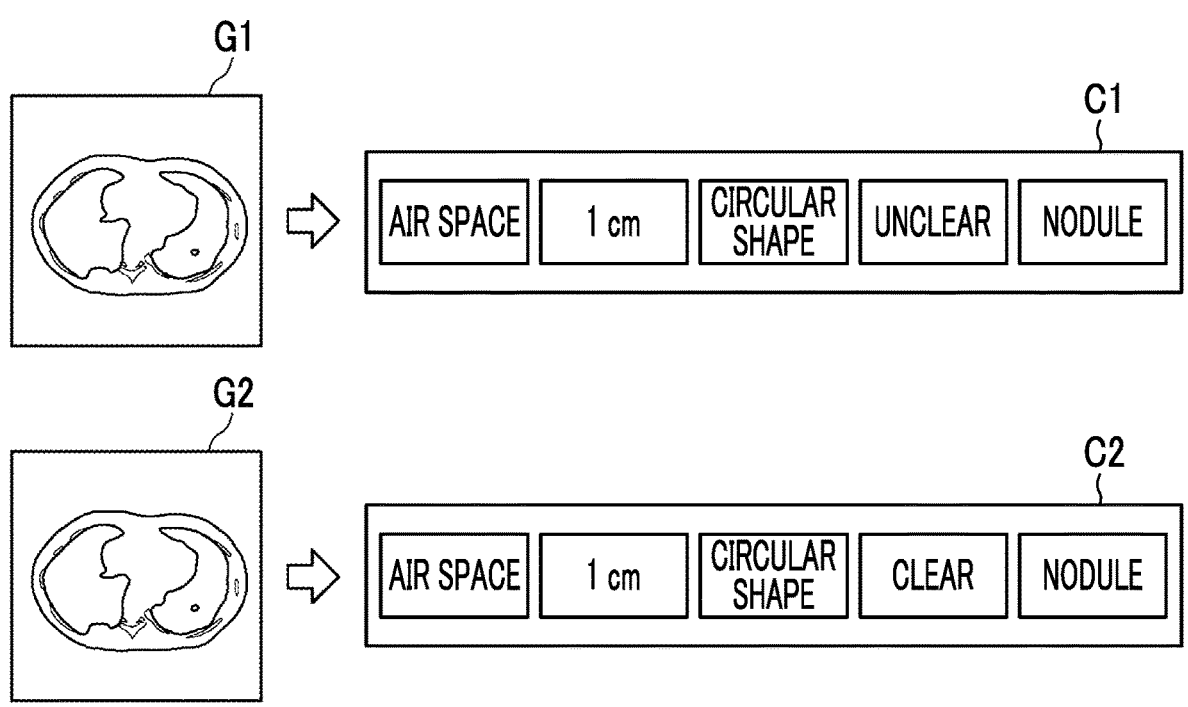
FIG. 3 is a diagram showing an example of feature information.

FIG. 3 is a diagram showing an example of feature information. As shown in FIG. 3, the first medical image G1 and the second medical image G2 are CT images of the lung field. Text data representing a plurality of findings of "air space", "1 cm", "circular shape", "unclear" and "nodule" are acquired from the first medical image G1 as the first feature information C1. In addition, text data representing a plurality of findings of "air space", "1 cm", "circular shape", "clear", and "nodule" are acquired from the second medical image G2 as the second feature information C2.

The sentence creation unit 23 compares the first feature information C1 and the second feature information C2 generated by the feature information acquisition unit 22, and creates a sentence representing a change between the first medical image G1 and the second medical image G2. For this purpose, the sentence creation unit 23 has a learned model 30 in which machine learning is performed so as to output the sentence indicating the change on the basis of first text data which is the first feature information C1 and second text data which is the second feature information C2. The learned model 30 is learned by the learning unit 25.

Figure 4:
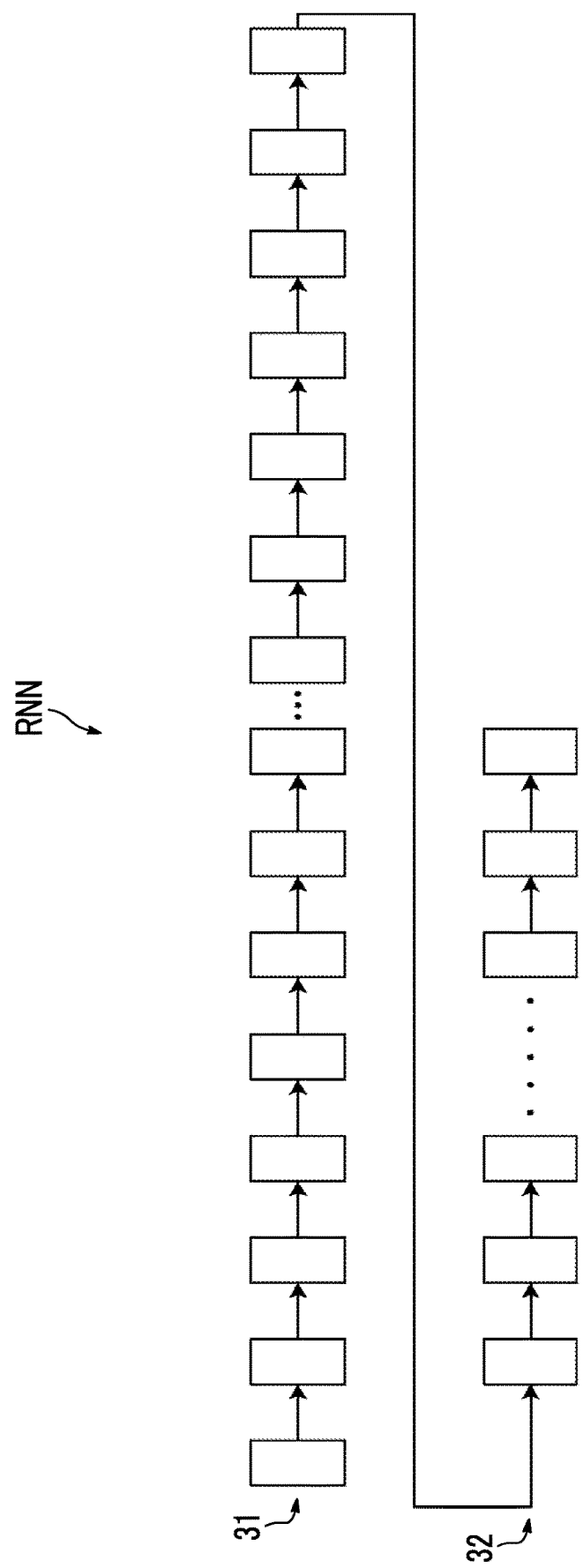
FIG. 4 is a diagram showing a schematic configuration of a recurrent neural network.

In the first embodiment, the learned model 30 is generated by learning a recurrent neural network in which learning is performed so as to create a sentence representing a change between two text data from two input text data. FIG. 4 is a diagram showing a schematic configuration of a recurrent neural network. As shown in FIG. 4, a recurrent neural network RNN has a plurality of input layers 31 and a plurality of output layers 32.

Findings represented by the first feature information C1 (that is, the first text data) and findings represented by the second feature information C2 (that is, the second text data) are input to each of the plurality of input layers 31. The output of the input layer 31 is input to the first layer in the plurality of output layers 32, and the words forming the sentence representing the change are sequentially output from each of the plurality of output layers 32. In the first embodiment, the learning unit 25 learns weight coefficients between the plurality of input layers 31 and the plurality of output layers 32 and mutual weight coefficients between the plurality of output layers 32 in the recurrent neural network RNN so as to sequentially output words constituting a sentence expressing a change on the basis of a correspondence relationship between the findings represented by the first feature information C1 and the findings represented by the second feature information C2. Thereby, the learned model 30 is generated.

Figure 5:
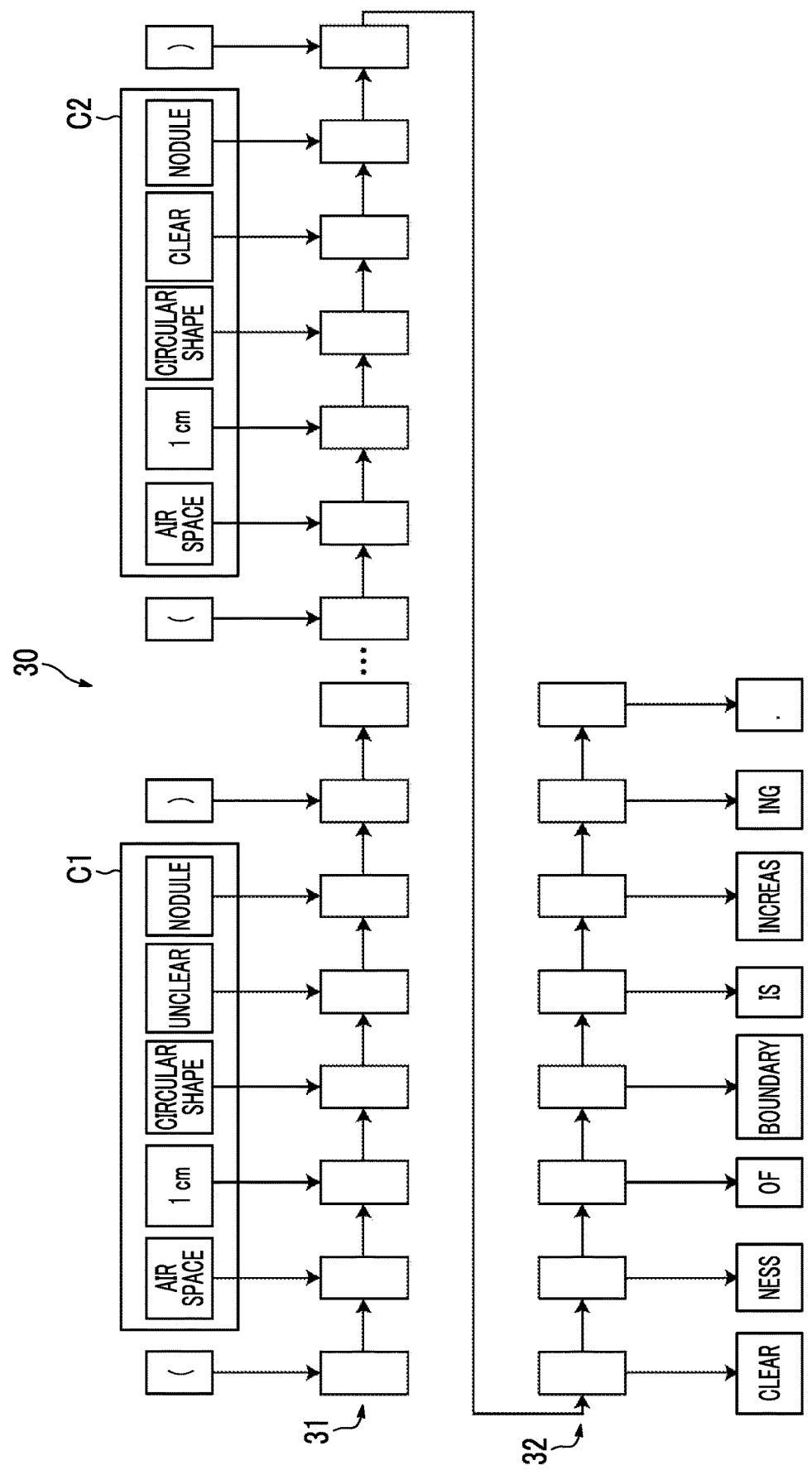
FIG. 5 is a diagram for explaining generation of a sentence representing a change by a learned model in the first embodiment.

FIG. 5 is a diagram for explaining generation of a sentence representing a change by the learned model 30 in the first embodiment. First, the first feature information C1 is input to the input layer 31 of the learned model 30.

Specifically, the findings of "air space", "1 cm", "circular shape", "unclear", and "nodule" are input to input layers 31 different from each other. In addition, the second feature information C2 is also input to the input layer 31. Specifically, the findings of "air space", "1 cm", "circular shape", "clear" and "nodule" are input to input layers 31 different from each other. It should be noted that parentheses representing delimiters of the feature information are input in the input layers before and after the input first and second feature information C1 and C2.

An output from the input layer 31 is input to the first layer of the output layer 32, and words constituting a sentence representing a change between the first feature information C1 and the second feature information C2 are sequentially output from each of the plurality of output layers 32. Specifically, words constituting a sentence of "clear", "of", "boundary", "is", "increasing", and "." are sequentially output from each of the plurality of output layers 32. Then, a sentence representing a change, "clearness of a boundary is increasing." is created by arranging the words in the order of the output from the output layer 32.

Figure 6:
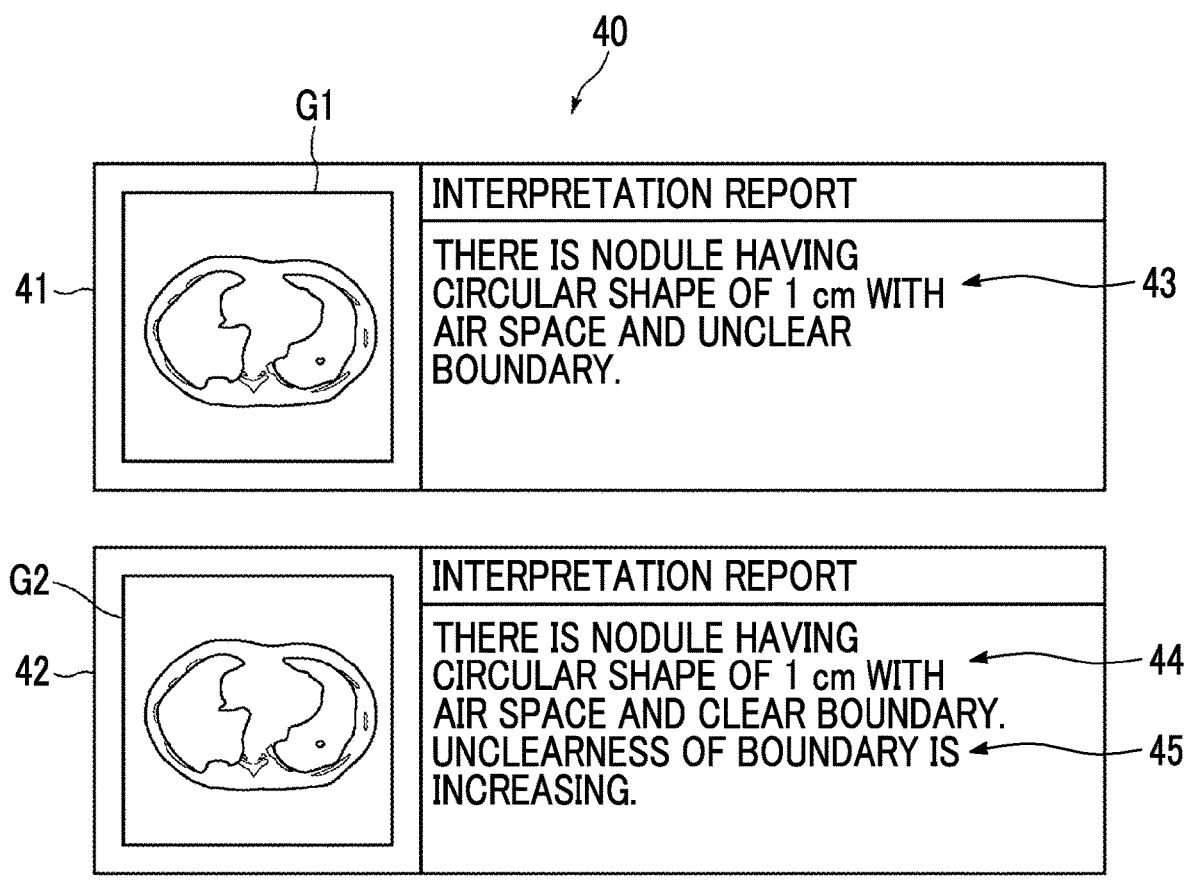
FIG. 6 is a diagram showing a display screen of a sentence showing a change.

The display control unit 24 causes the display unit 14 to display a sentence representing a change created by the sentence creation unit 23. FIG. 6 is a diagram showing a display screen of a sentence showing a change. As shown in FIG. 6, the display screen 40 includes an interpretation report 41 for the first medical image G1 and an interpretation report 42 for the second medical image G2. The interpretation report 41 for the first medical image G1 includes a sentence 43 of "there is a nodule having a circular shape of 1 cm with an air space and an unclear boundary.". The interpretation report 42 for the second medical image G2 includes a sentence 44 of "there is a nodule having a circular shape of 1 cm with an air space and a clear boundary.". It should be noted that the sentences 43 and 44 are created by the operator referring to and inputting the first feature information C1 and the second feature information C2. However, the medical document creation support apparatus 10 may be separately provided with a learning model for creating a sentence from the first and second feature information C1 and C2, and the sentences 43 and 44 may be created from the first and second features C1 and C2 by such a learning model.

Further, the interpretation report 42 for the second medical image G2 includes a sentence 45 representing a change in "unclearness of a boundary is increasing" created by the sentence creation unit 23.

It should be noted that the interpretation reports 41 and 42 are transmitted from the interpretation WS 3 to the interpretation report server 7 and registered in the interpretation report database 8.

Figure 7:
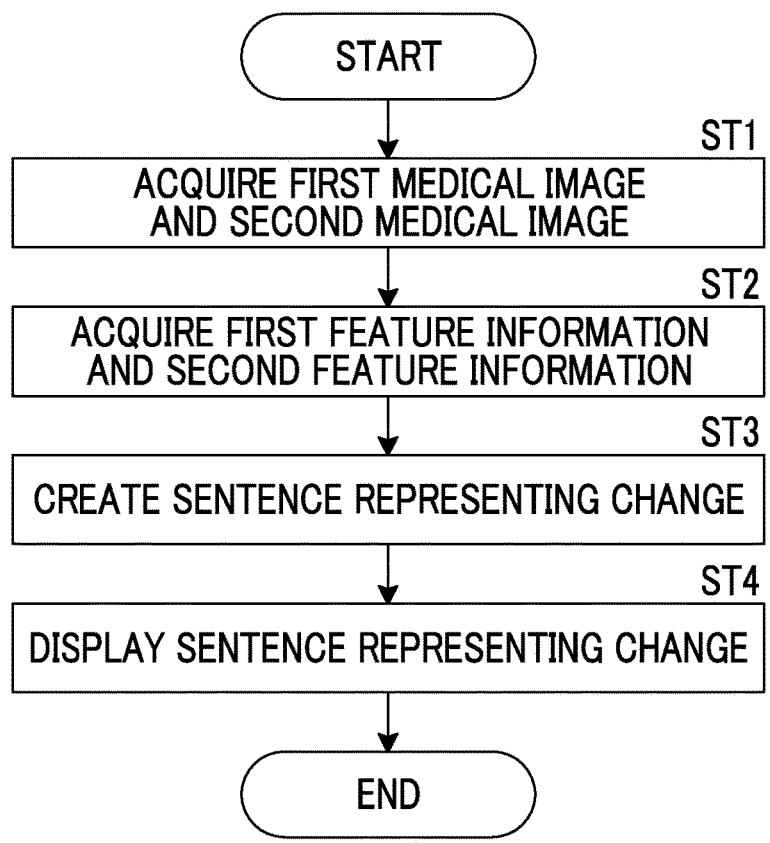
FIG. 7 is a flowchart showing processing performed in the first embodiment.

Next, the processing performed in the first embodiment will be described. FIG. 7 is a flowchart showing processing performed in the first embodiment. In a case where a medical image to be interpreted is input to the interpretation WS 3, and an instruction to create the interpretation report is given by an operator, the processing is started, and the image acquisition unit 21 acquires the first medical image G1 and the second medical image G2 having imaging times different from each other (step ST1). Next, the feature information acquisition unit 22 acquires the first feature information C1 on the first medical image G1 and the second feature information C2 on the second medical image G2 (step ST2). Next, the sentence creation unit 23 compares the first feature information C1 and the second feature information C2 generated by the feature information acquisition unit 22, and creates a sentence representing a change between the first medical image G1 and the second medical image G2 (step ST3). Then, the display control unit 24 displays the sentence representing the change on the display unit 14 (step ST4), and the processing is ended.

As described above, in the first embodiment, a medical document creation support method according to the present disclosure acquires the first feature information C1 on the first medical image G1 and the second feature information C2 on the second medical image G2 having an imaging time different from an imaging time of the first medical image G1, and compares the first feature information C1 and the second feature information C2 to create a sentence representing a change between the first medical image G1 and the second medical image G2. For this reason, it is possible to reduce the burden on the operator of creating medical documents such as the interpretation report particularly in a case of performing comparative interpretation, and as a result, the operator can efficiently create the medical documents.

It should be noted that in the first embodiment, the feature information acquisition unit 22 analyzes the first medical image G1 and the second medical image G2 to acquire the first feature information C1 and the second feature information C2, but the present invention is not limited to this. For example, for the first medical image G1 whose imaging time is earlier than that of the second medical image G2, an interpretation report has already been created and registered in the interpretation report database 8. Therefore, the feature information acquisition unit 22 inquires of the interpretation report server 7 whether or not the interpretation report is registered in the interpretation report database 8 with respect to the first medical image G1, and in a case of being registered, the feature information acquisition unit 22 acquires the interpretation report of the first medical image G1 from the interpretation report database 8 through the interpretation report server 7.

Figure 8:
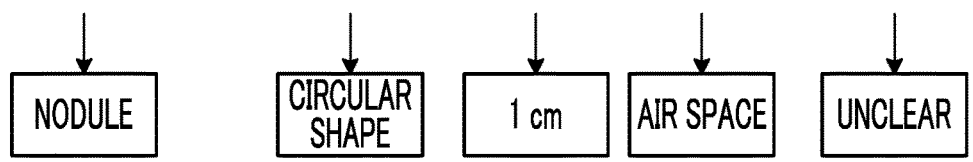
FIG. 8 is a diagram for explaining acquisition of the first feature information from an interpretation report.

In this case, the feature information acquisition unit 22 is provided with a finding extraction discriminator in which learning is performed to extract a finding from a sentence, and the feature information acquisition unit 22 extracts a finding from a sentence of the interpretation report in the finding extraction discriminator to acquire first feature information C1. FIG. 8 is a diagram for explaining acquisition of the first feature information C1 from an interpretation report. As shown in FIG. 8, it is assumed that the interpretation report is the sentence "there is a nodule having a circular shape of 1 cm with an air space and an unclear boundary.". In a case where this sentence is input, the finding extraction discriminator of the feature information acquisition unit 22 extracts findings of "air space", "1 cm", "circular shape", "unclear", and "nodule", thereby acquiring text data representing the findings as the first feature information C1.

It should be noted that the interpretation report may be registered in the interpretation report database 8 for the second medical image G2 as well. In this case, the feature information acquisition unit 22 may acquire the interpretation report for the second medical image G2 from the interpretation report database 8 through the interpretation report server 7, and acquire the second feature information C2 from the interpretation report for the second medical image G2.

In addition, in the first embodiment, the feature information acquisition unit 22 analyzes the first medical image G1 and the second medical image to acquire the first feature information C1 and the second feature information C2, but the present invention is not limited to this. For example, the operator may observe the first medical image G1 and the second medical image G2, and as a result, the findings input from an input unit 15 may be acquired as the first feature information C1 and the second feature information C2.

In addition, in the first embodiment described above, the first feature information C1 and the second feature information C2 are assumed as text data representing the findings, but the present invention is not limited to this. The first feature information C1 and the second feature information C2 may be the feature quantity representing the features of the first medical image G1 and the second medical image G2. Hereinafter, this will be described as the second embodiment.

Figure 9:
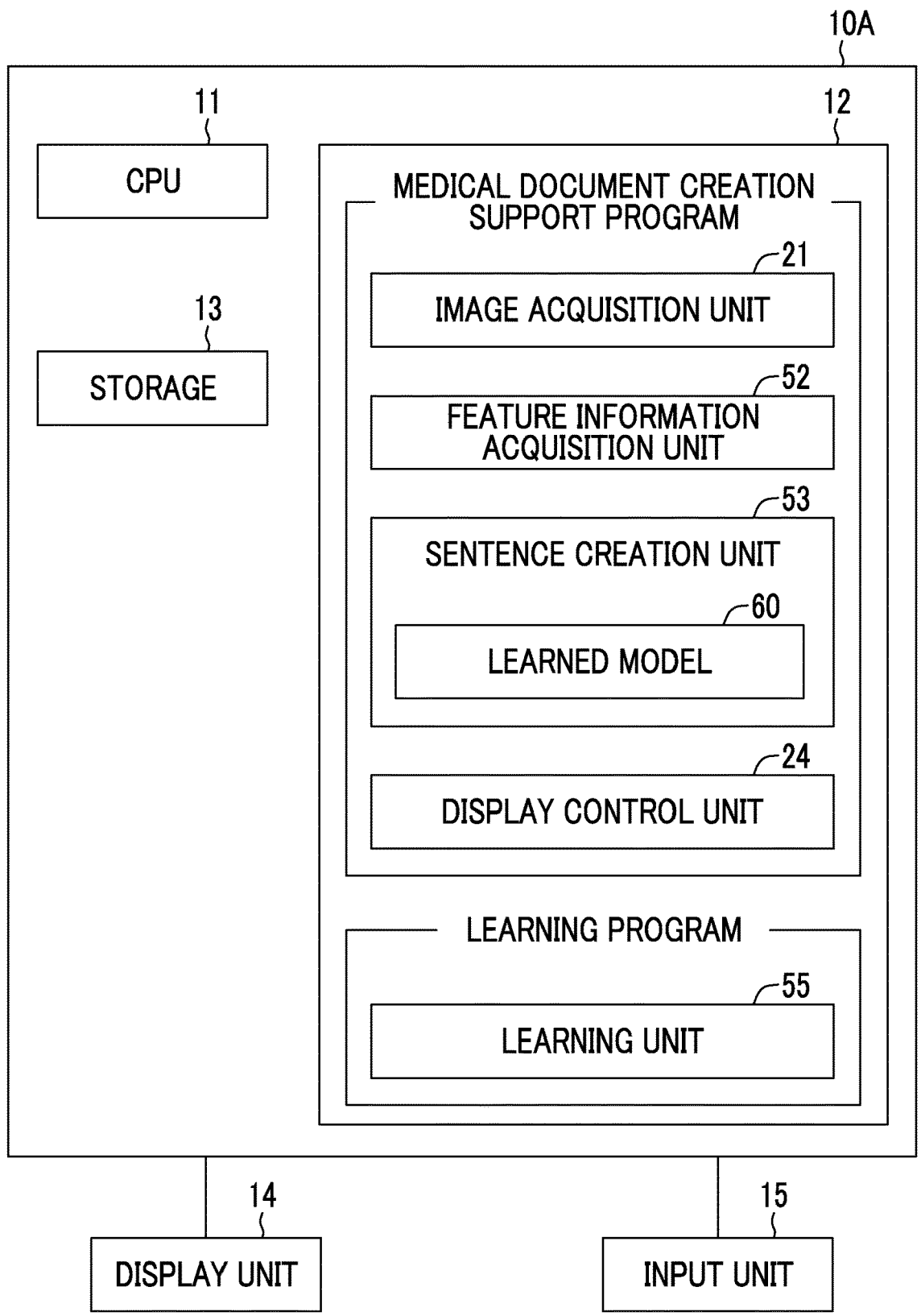
FIG. 9 is a diagram showing a schematic configuration of a medical document creation support apparatus according to the second embodiment.

FIG. 9 is a diagram showing a schematic configuration of a medical document creation support apparatus according to the second embodiment of the present disclosure. It should be noted that in FIG. 9, the same components as components in FIG. 2 are designated by the same reference numerals, and a detailed description thereof will be omitted. A medical document creation support apparatus 10A according to the second embodiment is different from the first embodiment in that it comprises a feature information acquisition unit 52, a sentence creation unit 53, and a learning unit 55 in place of the feature information acquisition unit 22, the sentence creation unit 23, and the learning unit 25 in the first embodiment.

The feature information acquisition unit 52 in the second embodiment acquires the feature quantity representing the feature of the first medical image G1 from the first medical image G1 as the first feature information C1. In addition, the feature quantity representing the feature of the second medical image G2 is acquired as the second feature information C2 from the second medical image G2. For this purpose, the feature information acquisition unit 52 comprises a discriminator in which machine learning is performed so as to extract the feature quantity from the first and second medical images G1 and G2. In the second embodiment, the discriminator consists of the neural network in which deep learning is performed so as to extract the feature quantity from the first and second medical images G1 and G2. It should be noted that the discriminator may input all the regions of the first and second medical images G1 and G2, but the discriminator may input only a region including the subject in the first and second medical images G1 and G2 or only a designated region in the first and second medical images G1 and G2.

It should be noted that at least one of information such as a location of the lesion in the medical image, a contrast of the lesion, a density of the lesion, or a differential value at a boundary between the lesion and another region can be used as the feature quantity. The discriminator included in the feature information acquisition unit 52 in the second embodiment performs learning to output these pieces of information as the feature quantity by inputting the medical image.

In addition, the feature information acquisition unit 52 may have only one discriminator and sequentially acquire the first feature information C1 and the second feature information C2 from the first medical image G1 and the second medical image G2, or may have two discriminators and acquire the first feature information C1 and the second feature information C2 in parallel from the first medical image G1 and the second medical image G2. In the latter case, a calculation time for acquiring the first and second feature information C1 and C2 can be shortened.

Also in the second embodiment, the discriminator may consist of, for example, a support vector machine, a convolutional neural network, a recurrent neural network, or the like, in addition to the neural network in which deep learning is performed.

The sentence creation unit 53 in the second embodiment compares the first feature information C1 and the second feature information C2 generated by the feature information acquisition unit 52, and creates a sentence representing a change between the first medical image G1 and the second medical image G2. For this purpose, the sentence creation unit 53 has a learned model 60 in which machine learning is performed so as to sequentially output words constituting a sentence representing a change on the basis of the first feature quantity which is the first feature information C1 and the second feature quantity which is the second feature information C2. The learned model 60 is learned by the learning unit 55.

Figure 10:
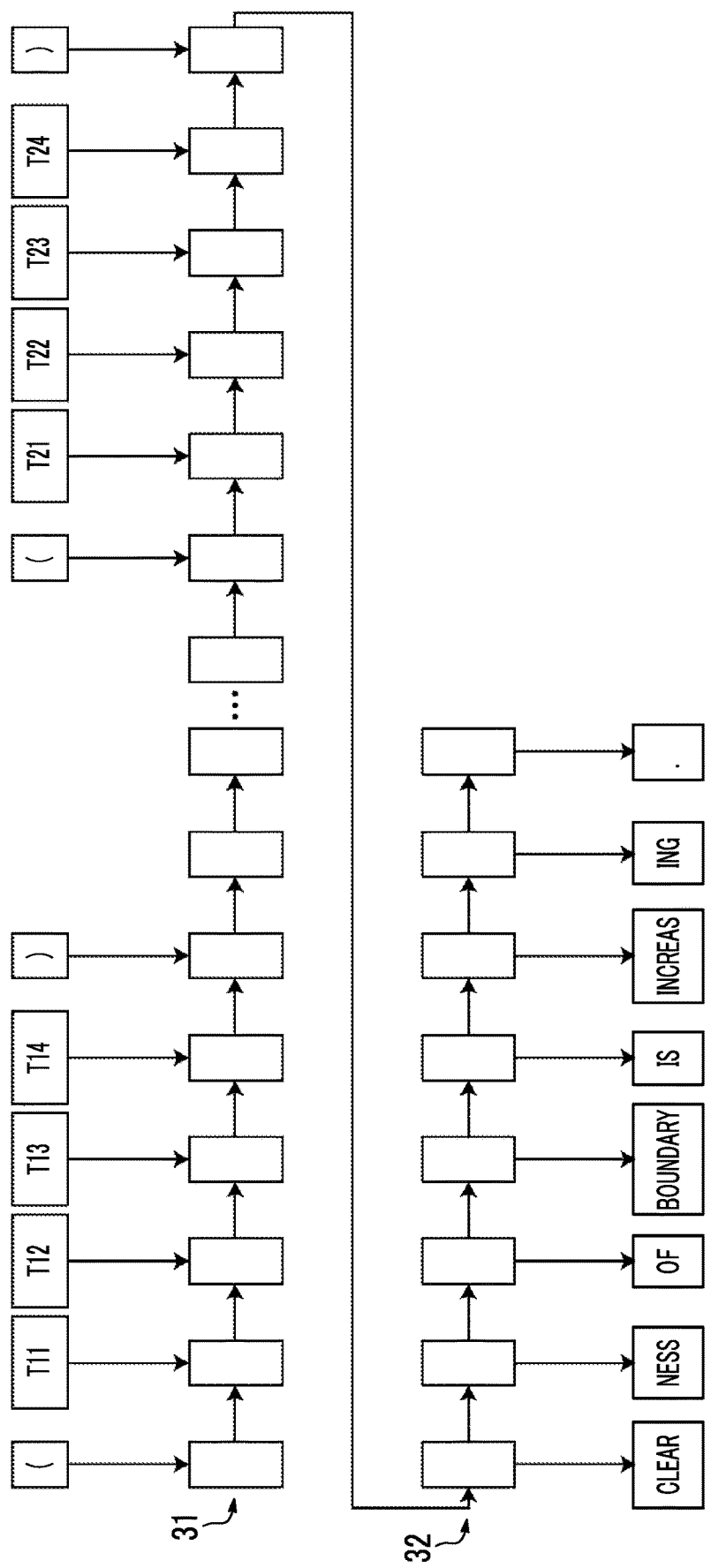
FIG. 10 is a diagram for explaining generation of a sentence representing a change by a learned model in the second embodiment.

In the second embodiment, the learned model 60 consists of the recurrent neural network in which learning is performed so as to create a sentence representing a change between two feature quantities from two input feature quantities. FIG. 10 is a diagram for explaining generation of a sentence representing a change by a learned model in the second embodiment. As shown in FIG. 10, the learned model 60, which is the recurrent neural network, has a plurality of input layers 61 and a plurality of output layers 62.

The information included in the feature quantity represented by the first feature information C1 and the information included in the feature quantity represented by the second feature information C2 are input to each of the plurality of input layers 61. The output of the input layer 61 is input to the first layer in the plurality of output layers 62, and the words forming the sentence representing the change are sequentially output from each of the plurality of output layers 62. In the second embodiment, the learning unit 55 learns weight coefficients between the plurality of input layers 61 and the plurality of output layers 62 and mutual weight coefficients between the plurality of output layers 62 in the recurrent neural network so as to sequentially output words constituting a sentence expressing a change on the basis of a correspondence relationship between the feature quantity represented by the first feature information C1 and the feature quantity represented by the second feature information C2. Thereby, the learned model 60 is generated.

In the second embodiment, information T11 to T14 included in the feature quantity represented by the first feature information C1 and information T21 to T24 included in the feature quantity represented by the second feature information C2 are input to each of the first input layers 61. It should be noted that parentheses representing delimiters of the feature information are input in the input layers before and after the input feature information C1 and C2.

An output from the input layer 61 is input to the first layer of the output layer 62, and words constituting a sentence representing a change between the first feature information C1 and the second feature information C2 are sequentially output from each of the plurality of output layers 62. Specifically, words constituting a sentence of "clear", "of", "boundary", "is", "increasing", and "." are sequentially output from each of the plurality of output layers 62. Then, a sentence representing a change, "clearness of a boundary is increasing." is created by arranging the words in the order of the output from the output layer 62.

In this way, a sentence representing a change between the first medical image G1 and the second medical image G2 can be created, similarly to the first embodiment, by using the first feature information C1 and the second feature information C2 as the feature quantity representing the features of the first medical image G1 and the second medical image G2. Accordingly, it is possible to reduce the burden on the operator of creating medical documents such as the interpretation report in a case of performing comparative interpretation, and as a result, the operator can efficiently create the medical documents.

In addition, in each of the above embodiments, the sentence creation units 23 and 53 have the learned models 30 and 60, and the learned models 30 and 60 create a sentence representing a change, but the invention is not limited to this. For example, the sentence creation units 23 and 53 may create the sentence representing the change by using conditional expressions. For example, in the first embodiment, individual findings included in the input first feature information C1 are compared with individual findings included in the second feature information C2 corresponding to the individual findings to determine whether or not a condition that words are different is satisfied, and in a case where the words are different, information representing a change of the words may be generated by assuming that there is a change between the first medical image G1 and the second medical image G2. In this case, the generated information representing the change may be embedded in a predetermined standard document to generate the sentence indicating the change.

For example, as in the first embodiment, it is assumed that the first feature information C1 is "air space", "1 cm", "circular shape", "unclear", and "nodule", and the second feature information C2 is "air space", "1 cm", "circular shape", "clear", and "nodule". In this case, in a case where the corresponding words are compared with each other, "unclear" and "clear" are different. Therefore, the information representing the change of the words is "clear". Here, in a case where the standard document is "XX is increasing.", a sentence representing a change such as "clearness is increasing." is created by inserting "clear" in "XX". Therefore, not only the learned model but also such a conditional expression may be used to create the sentence representing the change.

In addition, in each of the above embodiments, the medical document creation support apparatuses 10 and 10A comprise the learning units 25 and 55, and the medical document creation support apparatuses 10 and 10A perform learning of the recurrent neural network to generate the learned models 30 and 60 in the sentence creation units 23 and 53, but the present invention is not limited to this. For example, the interpretation WS 3 may comprise a learning apparatus separate from the medical document creation support apparatuses 10 and 10A, and the learning apparatus provided separately may perform learning of the recurrent neural network to generate the learned models 30 and 60. In addition, the learned models 30 and 60 may be generated by learning the recurrent neural network in an external analysis server or the like separate from the interpretation WS 3. In this case, in the interpretation WS 3, the medical document creation support apparatuses 10 and 10A are configured by installing the learned models 30 and 60.

In addition, in each of the above embodiments, the learned models 30 and 60 are generated by learning the recurrent neural network, but the present invention is not limited to this, and the learned models 30 and 60 may be generated by learning a neural network such as, for example, a support vector machine and a convolutional neural network.

In addition, in the first embodiment, the first and second feature information C1 and C2 are assumed as text data representing a plurality of findings, but the present invention is not limited to this, and may be text data representing one finding. For example, the first feature information C1 may be text data representing one finding "unclear", and the second feature information C2 may be text data representing one finding "clear".

In addition, in the second embodiment, the first and second feature information C1 and C2 are assumed as feature quantities consisting of a plurality of pieces of information, but the invention is not limited to this, and may be a feature quantity including only one piece of information.

Further, in the first embodiment, the feature information acquisition unit 22 of the medical document creation support apparatus 10 in the interpretation WS 3 analyzes the medical image, but the first feature information C1 and the second feature information C2 may be acquired by analyzing the medical image in an external analysis server or the like. In this case, the feature information acquisition unit 22 acquires the first feature information C1 and the second feature information C2 acquired outside.

In addition, in each of the above embodiments, the present disclosure is applied to the case of creating an interpretation report as a medical document, but the present disclosure can also be applied to the case of creating medical documents other than the interpretation report such as an electronic medical record and a diagnosis report.

What is claimed is:

1. A medical document creation support apparatus comprising at least one processor, wherein the processor is configured to:
    acquire first feature information on a first medical image and second feature information on a second medical image having an imaging time different from an imaging time of the first medical image, wherein the first feature information is first text data representing at least one finding based on the first medical image, and wherein the second feature information is second text data representing at least one finding based on the second medical image;
    compare the first feature information and the second feature information to create a sentence representing a change between the first medical image and the second medical image by using a learned model in which machine learning is performed; and
    output the sentence representing the change on the basis of the first text data and the second text data,
    wherein the learned model has a plurality of input layers to which each of at least one finding based on the first medical image and at least one finding based on the second medical image is input, and a plurality of output layers to which an output from the input layers is input and which output the sentence representing the change, in which the learned model being configured by a neural network in which weight coefficients between the plurality of input layers and the plurality of output layers are learned, and causing a computer to output the sentence representing the change so as to sequentially output a plurality of words constituting the sentence representing the change on the basis of a correspondence relationship between at least one finding based on the first medical image and at least one finding based on the second medical image in a case where the first text data and the second text data are input.

2. The medical document creation support apparatus according to claim 1, wherein the processor is configured to analyze at least one of the first medical image or the second medical image to acquire the first text data and the second text data.

3. The medical document creation support apparatus according to claim 1, wherein the learned model is further configured to learn mutual weight coefficients between the plurality of output layers.

4. The medical document creation support apparatus according to claim 1, wherein the processor is configured to acquire a feature quantity of the first medical image as the first feature information, and acquires a feature quantity of the second medical image as the second feature information.

5. The medical document creation support apparatus according to claim 1, wherein the processor is configured to display the sentence representing the change on a display.

6. A learned model comprising:
a plurality of input layers to which each of at least one finding based on a first medical image and at least one finding based on a second medical image having an imaging time different from an imaging time of the first medical image is input; and
a plurality of output layers to which an output from the input layers is input and which output a sentence representing a change between the first medical image and the second medical image,
wherein the learned model is configured by a neural network in which weight coefficients between the plurality of input layers and the plurality of output layers are learned, and in a case where the finding based on the first medical image and the finding based on the second medical image are input, the learned model causes a computer to output the sentence representing the change so as to sequentially output a plurality of words constituting the sentence representing the change on the basis of a correspondence relationship between at least one finding based on the first medical image and at least one finding based on the second medical image.

7. A learning apparatus for performing learning on a neural network to generate a learned model, the neural network having a plurality of input layers to which each of at least one finding based on a first medical image and at least one finding based on a second medical image having an imaging time different from an imaging time of the first medical image is input, and a plurality of output layers to which an output from the input layers is input and which output a sentence representing a change between the first medical image and the second medical image, the learning apparatus comprising at least one processor, wherein the processor is configured to:
perform learning for setting weight coefficients between the plurality of input layers and the plurality of output layers in the neural network so as to sequentially output a plurality of words constituting the sentence representing the change on the basis of a correspondence relationship between at least one finding based on the first medical image and at least one finding based on the second medical image in a case where the finding based on the first medical image and the finding based on the second medical image are input.

8. A medical document creation support method comprising:
acquiring first feature information on a first medical image and second feature information on a second medical image having an imaging time different from an imaging time of the first medical image, wherein the first feature information is first text data representing at least one finding based on the first medical image, and wherein the second feature information is second text data representing at least one finding based on the second medical image; and
comparing the first feature information and the second feature information to create a sentence representing a change between the first medical image and the second medical image by using a learned model in which machine learning is performed; and
outputting the sentence representing the change on the basis of the first text data and the second text data,
wherein the learned model has a plurality of input layers to which each of at least one finding based on the first medical image and at least one finding based on the second medical image is input, and a plurality of output layers to which an output from the input layers is input and which output the sentence representing the change, in which the learned model being configured by a neural network in which weight coefficients between the plurality of input layers and the plurality of output layers are learned, and causing a computer to output the sentence representing the change so as to sequentially output a plurality of words constituting the sentence representing the change on the basis of a correspondence relationship between at least one finding based on the first medical image and at least one finding based on the second medical image in a case where the first text data and the second text data are input.

9. A learning method for performing learning on a neural network to generate a learned model, the neural network having a plurality of input layers to which each of at least one finding based on a first medical image and at least one finding based on a second medical image having an imaging time different from an imaging time of the first medical image is input, and a plurality of output layers to which an output from the input layers is input and which output a sentence representing a change between the first medical image and the second medical image, the learning method comprising:
performing learning for setting weight coefficients between the plurality of input layers and the plurality of output layers in the neural network so as to sequentially output a plurality of words constituting the sentence representing the change on the basis of a correspondence relationship between at least one finding based on the first medical image and at least one finding based on the second medical image in a case where the finding based on the first medical image and the finding based on the second medical image are input.

10. A non-transitory computer-readable storage medium that stores a medical document creation support program for causing a computer to execute:
a procedure for acquiring first feature information on a first medical image and second feature information on a second medical image having an imaging time different from an imaging time of the first medical image, wherein the first feature information is first text data representing at least one finding based on the first medical image, and wherein the second feature information is second text data representing at least one finding based on the second medical image;
a procedure for comparing the first feature information and the second feature information to create a sentence representing a change between the first medical image and the second medical image by using a learned model in which machine learning is performed; and a procedure for outputting the sentence representing the change on the basis of the first text data and the second text data, wherein the learned model has a plurality of input layers to which each of at least one finding based on the first medical image and at least one finding based on the second medical image is input, and a plurality of output layers to which an output from the input layers is input and which output the sentence representing the change, in which the learned model being configured by a neural network in which weight coefficients between the plurality of input layers and the plurality of output layers are learned, and causing a computer to output the sentence representing the change so as to sequentially output a plurality of words constituting the sentence representing the change on the basis of a correspondence relationship between at least one finding based on the first medical image and at least one finding based on the second medical image in a case where the first text data and the second text data are input.

11. A non-transitory computer-readable storage medium that stores a learning program for causing a computer to execute a process of performing learning on a neural network to generate a learned model, the neural network having a plurality of input layers to which each of at least one finding based on a first medical image and at least one finding based on a second medical image having an imaging time different from an imaging time of the first medical image is input, and a plurality of output layers to which an output from the input layers is input and which output a sentence representing a change between the first medical image and the second medical image, and the learning program causing the computer to execute a learning procedure for setting weight coefficients between the plurality of input layers and the plurality of output layers in the neural network so as to sequentially output a plurality of words constituting the sentence representing the change on the basis of a correspondence relationship between at least one finding based on the first medical image and at least one finding based on the second medical image in a case where the finding based on the first medical image and the finding based on the second medical image are input.

* * * * *